United States Patent [19]
Chin et al.

[11] Patent Number: 5,434,327
[45] Date of Patent: Jul. 18, 1995

[54] PROCESS FOR DIMERIZING PROPYLENE AND FOR CONVERTING HEXENES INTO ETHERS

[75] Inventors: Arthur A. Chin, Cherry Hill, N.J.; Stephen S. F. Wong, Singapore, Singapore

[73] Assignee: Mobil Oil Corporation, Fairfax, Va.

[21] Appl. No.: 953,402

[22] Filed: Sep. 29, 1992

Related U.S. Application Data

[63] Continuation-in-part of Ser. No. 729,109, Jul. 12, 1991, abandoned.

[51] Int. Cl.$^6$ .................. C07C 2/08; C07C 41/06
[52] U.S. Cl. ..................... 585/533; 585/324; 585/329; 585/510; 585/520; 568/697
[58] Field of Search ............. 585/310, 324, 329, 510, 585/520, 533; 568/697

[56] References Cited

U.S. PATENT DOCUMENTS 3,992,466 11/1976 Plank et al. .............. 260/671 C
4,324,940 4/1982 Dessau ..................... 585/466
4,886,925 12/1989 Harandi ................... 585/331

FOREIGN PATENT DOCUMENTS 0047906 3/1982 European Pat. Off. .

OTHER PUBLICATIONS

Industrial & Engineering Chemistry: 'Tertiary Alkyl Ethers', 1936, vol. 28, pp. 1186–1188.

Primary Examiner—P. Achutamurthy
Attorney, Agent, or Firm—Alexander J. McKillop; Dennis P. Santini; Laurence P. Hobbes

[57] ABSTRACT

Hexenes are produced when propylene is catalytically converted under moderate conditions over chosen small pore zeolite catalysts having small 10-membered ring openings. These chosen catalysts are ZSM-22, ZSM-23, ZSM-35, and ZSM-48. They are unexpectedly effective to dimerize a substantially ethylene-free propylene-rich stream to form mainly hexene isomers, a major portion of which isomers are tert-isohexenes, without making a substantial amount of trimer or other byproducts. The feed is preferably at least 60% by weight, the remainder being alkanes, mainly propane, and the olefins being limited to less than 5 mol % ethylene and less than 5 mol %, preferably less than 2 mol %, of $C_4=+$ (mainly butenes). Because propane in the feed is essentially unaffected, plural reactors in series may be used to avoid recycling unreacted propylene with propane to the dimerization reactor. The reactors thus allow using a mixed propylene-propane stream without need for a superfractionator to make the desired separation. Etherification is effective because of the high tert-isohexene content of the dimer product. Non-tertiary hexenes from the etherification reactor may be recycled to the dimerization reactor to benefit from the ability of the chosen catalyst to isomerize the non-tert-hexenes to tert-isohexenes on a substantially mol for mol basis without making other products typically in equilibrium in the isomerized effluent of other zeolite catalysts such as ZSM-5.

17 Claims, 1 Drawing Sheet

PROCESS FOR DIMERIZING PROPYLENE AND FOR CONVERTING HEXENES INTO ETHERS

Cross-Reference to Related Applications

This application is a continuation-in-part of U.S. application Ser. No. 07/729,109, filed Jul. 12, 1991, now abandoned, the entire disclosure of which is expressly incorporated herein by reference.

BACKGROUND OF THE INVENTION

1. Field of the Invention

This invention relates to a process for the catalytic dimerization of propylene to provide a dimerized product in an effluent which is predominantly hexenes. The major portion (by weight) of the hexenes are not only isohexenes, but more specifically, tert-isohexenes. By "isohexenes" we refer to all branched chain hexenes and not specifically to only those having a (CH3)2—CH— group at the end of a hydrocarbon chain. By "tert-isohexenes" we refer to those isohexenes having an etherifiable C atom, namely, a C atom with a double bond, the C atom connected to two other C atoms, for example

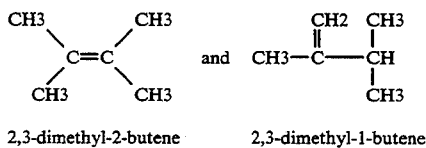

2,3-dimethyl-2-butene     2,3-dimethyl-1-butene

The process employs the acidic form of certain natural or synthetic porous crystalline materials or zeolites as the catalyst, but only those more constrained small pore (sometimes generically referred to as "intermediate pore") zeolites having 10-membered rings, namely ZSM-22, ZSM-23, ZSM-35, and ZSM-48, which we found to have unique characteristics under the process conditions described herebelow. Such catalysts are therefore referred to herein as "chosen catalysts".

Though other catalysts may be synthesized to duplicate the unique shape selectivity of the foregoing "chosen catalysts", these chosen catalysts are the only ones we know will provide the peculiar catalytic activity which is the cornerstone of my process. Such activity is attributable in large part to the constraint index (CI) and sorption characteristics of the chosen catalysts, as will be described hereinafter.

The dimer from the effluent, referred to herein as "dimerized product" because it contains a major portion by weight of hexene isomers (dimer), is recovered with unexpected ease. The ease with which the dimer is obtained is fortuitous because the saving in processing costs provides one with the option either to blend it (the dimer) directly into "base" gasoline, or, to etherify all, or a portion of the dimer with lower $C_1$-$C_5$ aliphatic alcohols, including secondary alcohols. The latter option is especially advantageous because the etherification reaction proceeds apace and with gratifying selectivity. The surprising economic effectiveness of the etherification process is directly attributable to the peculiar property of any chosen catalyst to isomerize non-tertiary hexenes to tert-hexenes and tert-isohexenes without producing an equilibrium mixture of common carbon number components, as will be explained herebelow.

The ease with which the etherification reaction proceeds, in turn, allows the etherate to be blended into gasoline. When "base" ($C_5^=+$) gasoline (RON 93.7; MON 79.1, for example) is boosted with the etherate of isohexenes, and of tert-isohexenes in particular, gasoline so blended has a highly useful octane number, and a relative low RVP (Reid Vapor Pressure) with respect to base gasoline.

It will be readily recognized that ethers of tertiary hexenes have a wide variety of uses, but one can only aspire to use them as a constituent of gasoline if the difficulty of making them economically can be overcome.

2. The Relevant Prior Art

The past decade has seen a great emphasis on upgrading light monoolefins by converting them to more valuable, higher molecular weight products. In particular, the olefin interconversion process converts $C_2+$ monoalkenes into an equilibrium olefin mixture under conditions which maximize the formation of $C_4$ and $C_5$ iso-olefins (isobutene, 2-methyl-1-butene, and 2-methyl-2-butene). These tert-olefins react readily with methanol to form methyl ethers, namely methyl tert-butyl ether (MTBE) and tert-amyl methyl ether (TAME) which are components for high octane gasoline.

The olefin interconversion process must cope with undesirable side reactions which yield aromatics and paraffins, the presence of which is acutely noticed at the relatively high temperatures (>700° F.) at which $i$-$C_4^=$ and $i$-$C_5^=$ formation is thermodynamically favored. Moreover, since the MOI process produces a near-equilibrium mixture of $C_2$-$C_{13}$ olefins, it is necessary, in the prior art processes, to recycle the $C_6+$ product to increase the selectivity to the desired $C_4$ and $C_5$ iso-olefins. But recycling the $C_6+$ product which results in cracking and isomerization reactions can vitiate the economics of the recycle. Furthermore, the presence of H-transfer products and cycloolefins in the recycle can reduce overall yields under recycle conditions to the point where the economics of the process relegate it to be too demanding to be commercial.

In our invention, in addition to producing a predominantly hexene-containing dimerized product, more than 50% by weight of which hexenes are tert-isohexenes, our process has another unique functional characteristic. Process economics of etherification of tert-isohexenes dictate that unreacted $C_6^=$ be recycled to the dimerization reactor (because they were not etherified). The chosen catalysts used in our process are uniquely able to isomerize the recycle to generate a mixed stream of tert-isohexenes and hexenes essentially in equilibrium with each other, the molar amount of the $C_6$s in the mixed stream being the same as that of the $C_6$s in the recycle stream. This isomerization of $C_6^=$ olefins on a mol for mol basis has not been documented or otherwise substantiated, to our knowledge, for any zeolite catalyst. As a result of this unique activity of the chosen catalysts, there is essentially no loss of valuable $C_6^=$ due to the formation of undesirable byproducts.

Though unreacted oligomers from prior art etherification reactors are recycled to the oligomerization reactor, the recycle stream in such prior art processes does not produce isomerized olefins in equilibrium with the unreacted recycled monoolefins on an essentially mol for mol basis. The foregoing facts about recycling unetherified olefins to the oligomerization reactor is implicitly emphasized in U.S. Pat. No. 4,886,925 to Harandi. The conversion of a feedstock rich in $C_2+$ n-alkenes using a medium pore zeolite results in a first stream of $C_4$-$C_6$ alkenes rich in isoalkenes, a second stream of $C_7+$ olefinic gasoline boiling range hydrocarbons, and a third stream of unconverted hydrocarbons. It is commercially disadvantageous to deal with three such streams if the goal is to produce tert-alkyl ethers economically.

Clearly, it would be far more advantageous to oligomerize an olefin stream to produce only tert-isoalkenes which could then be converted to the desired ethers with great economy. But nothing in the prior art suggests how one might tailor a zeolite-catalyzed oligomerization process to produce a major proportion by weight of any tert-isoalkenes. In particular, there is no suggestion that one might efficiently oligomerize a substantially pure propylene stream to produce a major proportion of tert-isohexenes in the effluent, irrespective of the particular characteristics of the catalyst which may be used to do so.

A particular process described in U.S. Pat. No. 4,899,014 to Avidan, Johnson and Soto, discloses a process for conversion of a propylene-rich feedstock which contains at least 2 mol % ethylene into isobutane and $C_5+$ gasoline. Another oligomerization process described in U.S. Pat. No. 4,873,385 to Avidan and Johnson describes the conversion of a propylene-rich feedstock to distillate using a wide variety of ZSM catalysts. Any ZSM-5 type catalyst having a constraint index (CI) in the range from 1 to 12, including ZSM-22, ZSM-23, ZSM-35, and ZSM-48, is said to be effective. The temperature and pressure at which this conversion occurs is stated to be in the range from about 315° C. to 510° C., and from 400 to 2500 kPa, respectively. Such conditions generally encompass the operating conditions for the olefin interconversion process, as well as the process of this invention. Yet the '014 process produces a gasoline range product containing at least 6% isobutane; and, the '385 process produces about 20% by weight of distillate per pass. There is essentially no distillate produced in the dimerization of a propylene-rich feedstock in our process because oligomerization to $C_9+$ is less than 10% by weight of the effluent, and there is less than 6% isobutane.

There would seem to be good and sufficient reason to believe that, knowing the scope of the foregoing '925, '014 and '385 disclosures, one could use substantially the same catalyst, under substantially the same process conditions, to provide substantially the same result. If one did so, the result would be the formation of isobutane and $C_5+$ hydrocarbons (in the '014 process), or, three streams which have to be dealt with (in the '925 process), or, gasoline and distillate. All such results are far removed from the goal of making a dimerized product, the major portion by weight of which is the dimer (hexene isomers); and, the more important goal—a dimer in which a major portion by weight of the hexenes is present as tert-isohexenes (in the effluent of an oligomerization reactor).

Despite the foregoing reasonable expectation, the best mode of the process was found to be with a substantially C3 feed-stream, containing a major portion by weight of $C3=$ and substantially free of ethylene, which was found to make the essential difference in the production of the dimerized product. By "substantially free of ethylene" we refer to a stream which has less than 5 mol % ethylene in it, preferably less than 2 mol %.

The dimerized product was produced in our process over only a few of the many ZSM-5 type catalysts having 10-membered rings suggested in the art as being effective oligomerization catalysts. ZSM-5 is disclosed in U.S. Pat. No. 3,702,886 and U.S. Pat. No. Re. 29,948.

Particularly because the activity of such catalysts is so closely tied to their physical structure, it is surprising that only some of those ZSM catalysts which have a constraint index (CI) in the range from 3 to about 10, and specifically only a few having a CI in the range from 3.5 to 9.1, have been found useful in the process claimed herein. ZSM-5 itself, with a CI of 6, is not. ZSM-22 with a CI of 7.3, is.

For the same reason, namely, that the catalytic activity of such catalysts is so closely tied to their physical structure and shape selectivity, it is surprising that only some (the chosen) ZSM catalysts are able to provide the unique physico-chemical characteristics found to be effective in my dimerization process, though others have about the same pore size (largest pore size in the range from about 4.2 Å×5.5 Å to about 5.3 Å×5.6 Å) and a sorption rate, measured at 100° C., for n-hexanes in the relatively narrowly defined range from about 25–50 $\mu L/(gm)(sec^{0.5})$ ($\mu L$=microliters). ZSM-5 itself, which has a largest pore size of 5.3 Å×5.6 Å and a sorption rate of 50 $\mu L/(gm)(sec^{0.5})$ is not. ZSM-48 which has the same largest pore size, namely 5.3 Å×5.6 Å, and a sorption rate of 32 $\mu L/(gm)(sec^{0.5})$, is.

In view of the fact that the dimerized product sought is tert-isohexenes which are large molecules about the same size as 3-methylpentane, one would expect that a zeolite with a large pore size, like ZSM-5, which exhibits a relatively high sorption rate of 3-methylpentane, would be far more effective dimerization catalysts, with better selectivity, than one with a relatively smaller pore size, like ZSM-35, ZSM-22 or ZSM-23. Yet ZSM-5 is not even closely competitive for the purpose at hand.

The foregoing peculiar relationship of sorption rate to the catalytic activity of the chosen catalysts, extends to the equilibrium sorption capacity ("ESC" for brevity, cc/g) they exhibit, as will be described hereafter.

Prior art oligomerization catalysts were never primarily concerned with producing a dimerized product with a substantially $C3=$ rich feed. The problem they solved was not how to make dimer efficiently, but how to oligomerize $C3=$s to any oligomerization product efficiently. Since there was no reason for picking and choosing amongst the many effective oligomer-ization catalysts, the prior art provided no clue as to which criteria determined the unique effectiveness of any specific ZSM or related catalyst for the purpose at hand, namely dimerization. Since the narrow problem of making a major proportion by weight of $C_6=$ dimer (for over-riding economic reasons), was never isolated from the overall problem of making oligomerization product, prior workers found no reason to consider the cause of the narrow problem. It is therefore not surprising that they never suggested a solution to a problem they did not have.

Not at all coincidentally, despite the well-known fact that the economics of operating an oligomerization process is very much an essential facet, if not the most important facet, of its success, it is worth noting that the economic bottlenecks of the prior art processes are not highlighted. The economics of our process relies largely upon operating with a propylene-rich feed, essentially free of higher and lower olefins, containing at least 60% propylene and more preferably at least 80%, without benefit of a $C3=/C3$ superfractionator. Because our dimerization reactor ignores the presence of propane, it discharges the function of the missing superfractionator even if a single reactor is used, and a portion of the dimerized product stream containing unreacted propylene and incoming propane, is recycled. More preferably, since the per pass conversion of $C_3=$ and selectivity to hexenes are each more than 30% and preferably greater than 50%, the use of plural reactors in series, effectively converts essentially all propylene and obviates recycling the remaining propylene and propane. Thus, with plural reactors in series, the only recycle stream to the dimerization reactor can be unetherified hexenes.

SUMMARY OF THE INVENTION

It has been discovered that chosen small pore zeolite catalysts having small 10-membered ring openings, namely ZSM-22, ZSM-23, ZSM-35, and ZSM-48, are unexpectedly effective to dimerize a substantially ethylene-free propylene-rich stream to form mainly hexene isomers, a major portion of which isomers are tert-isohexenes, without making a substantial amount of trimer or other byproducts. By "propylene-rich" stream we refer to one in which the concentration of propylene is at least 60% by weight, the remainder being alkanes, mainly propane, and the olefins being limited to less than 5 mol % ethylene and less than 5 mol %, preferably less than 2 mol %, of $C_4 =+$ (mainly butenes).

It is therefore a general object of this invention to provide a highly selective process for the dimerization of a substantially ethylene-free propylene-rich feed stream in contact with a specified small-pore catalyst, in a fixed bed or fluid bed reaction zone, under widely variable process conditions. The severity of such conditions may vary widely from being lower than those normally used for lower olefin ($C_2-C_4=$) oligomerization, to higher than is normally used, yet they generate a unique dimerized product containing a major amount by weight of hexene isomers. This dimerized product in turn, contains a major proportion by weight of tert-isohexenes, and typically, also less than about 15% $C_9+$ ($C_9$ and higher) oligomers The high yield of $C_6=$ dimer (more than 50% by wt) and the "make" of such a small amount of byproducts, allows one to simply flash away the monomeric components from the dimerized product to recover it. The easily-separated tert-isohexene-rich stream is exceptionally well-suited for conversion to ethers.

It has also been discovered that, under dimerization conditions, a chosen catalyst has the unique ability to isomerize non-tert-hexenes to produce essentially only other hexene isomers, particularly tert-isohexenes, in equilibrium with the $C_6$ isomers generated, instead of a common carbon number and olefin isomer distribution characteristic of ZSM-5 catalyst.

It is therefore a specific object of this invention to provide chosen catalysts, namely ZSM-22, ZSM-23, ZSM-35, and ZSM-48, which have been found uniquely effective (i) to dimerize a propylene-rich feedstream under low-to-moderate pressure from 0.1–10 atm, a temperature in the range from 230° C.–455° C. (450° F.–850° F.), and WHSV (weight hourly space velocity) in the range from 0.1–50, and (ii) to isomerize non-etherifiable olefins, including straight-chain olefins, to produce isoolefins with an etherifiable C atom in equilibrium with olefins without one (an etherifiable C atom), and without substantially cracking the hexenes or generating higher molecular weight byproducts.

It is another specific object of this invention to provide at least one, and preferably, plural dimerization reactors in series, to separate unwanted propane from propylene which is to be converted to a dimerized product, the major $C_6=$ monoolefinic content of which has a tert-isohexene structure; and, to maximize reactor productivity by using two or more reactors in series so as to avoid recycling propane to the dimerization reactor.

It has also been discovered that the unique selectivity of the chosen catalysts under moderate operating conditions to produce either a per pass conversion of $C_3=$ at least 40%, preferably greater than 60%, or, a selectivity to tert-hexenes of at least 30%, preferably greater than 50%, or, each greater than 0%, coupled with the catalysts' ability to isomerize non-etherifiable hexenes in an equilibrium mixture of etherifiable and non-etherifiable hexenes on a mol for mol basis, allows the dimerization process (referred to as a first root process) to be coupled with an etherification process (a second root process) in a symbiotic relationship not realized in any integrated oligomerization and etherification process in the prior art.

It is therefore a general object of this invention to provide an integrated process for the production of ethers of tert-hexenes, a major portion of which ethers are those of tert-isohexenes, comprising, a first root process comprising dimerizing a propylene-rich stream to form a tert-isohexene-rich stream, and, a second root process comprising etherifying tert-isohexenes with a lower primary or secondary $C_1-C_5$ aliphatic alcohol to form ethers; said first root process comprising, (a) feeding a propylene-rich feed essentially free of lower and higher olefins into a dimerization reaction zone, (b) contacting said feed with a catalyst characterized by shape selectivity of a small-pore zeolite having a 10-membered ring structure, said zeolite being selected from the group consisting of ZSM-22, ZSM-23, ZSM-35 and ZSM-48, at a pressure in the range from 0.1 to 10 atm., and a temperature in the range from 232° C.–426° C. (450°–800° F.); (c) flowing said feed through said reaction zone at a weight hourly space velocity (WHSV) on an olefin basis in the range from 0.1 to 30 hr−1; and, (d) converting at least 60% by weight of said propylene to a dimer product containing a major proportion by weight of hexene isomers more than 50% by weight of which isomers are tert-isohexenes; and, said second root process comprising, (e) reacting said tert-isohexene-rich stream with said alcohol in the presence of an acid etherification catalyst under reaction conditions effective to produce a mixture of tert-alkyl ethers; (f) recovering an ether-rich effluent essentially free of propylene, unreacted alkenes and unreacted alcohol; and, (g) recovering said mixture of tert-alkyl ethers.

It is a further specific object of this invention to recover unreacted hexene isomers from the effluent of the etherification reaction zone, and recycle the isomers to the oligomerization reactor to generate more tert-hexenes.

BRIEF DESCRIPTION OF THE DRAWINGS

The foregoing and other objects and advantages of the invention will be more fully understood in conjunction with the following detailed description of the invention along with the attached drawings in which like numerals refer to like structural components, and in which.

DETAILED DESCRIPTION OF PREFERRED EMBODIMENTS

Figure 1:
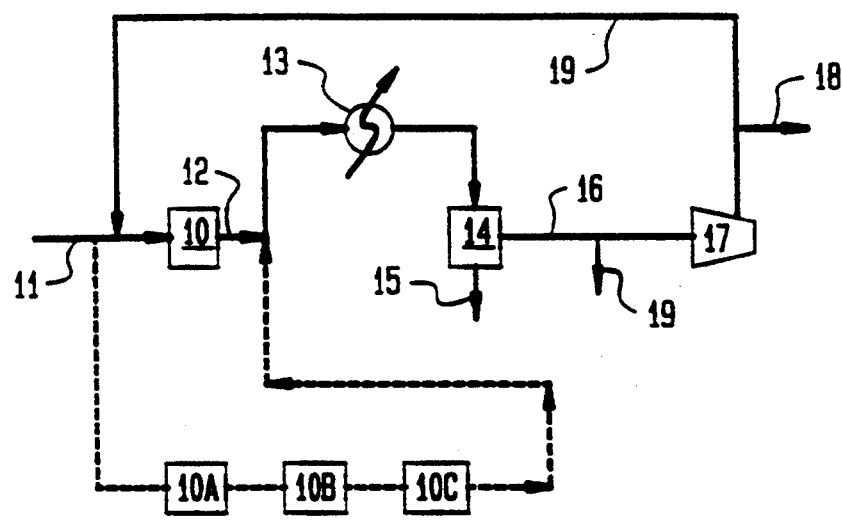
FIG. 1 is a diagrammatic flowsheet illustrating the basic process using dimerization reaction zone for the catalytic dimerization of an olefinic feedstream in which propylene is essentially the only olefin, and containing no more than about 40% by weight of propane and other lower alkanes.

The chosen catalysts identified herein, produced by known zeolite technology, have been found to be especially effective because of their peculiar physico-chemical and shape selective characteristics. They belong to a group of siliceous materials having pores of relatively smaller size but a similar pore geometry, namely, 10-membered rings. Only a few members of this group of catalysts are effective for the purpose at hand. For example, the known oligomerization of lower olefins by ZSM-5 (see "Conversion of $C_2$-$C_{10}$ to Higher Olefins over Synthetic Zeolite ZSM-5" by W. E. Garwood in Intrazeolite Chemistry, ACS Symposium Series, ACS 1983) does not meet the shape selective requirements for the process claimed herein despite its apparently suitable pore size at the upper end of the effective range of "largest pore size" for the catalysts I have found to be effective.

To help focus the significance of pore size, and the unexplained ineffectiveness of one catalyst (ZSM-5) compared with the effectiveness of another (ZSM-48) having the same pore size, the largest pore sizes are set forth in Table I herebelow.

TABLE I

| Catalyst | Largest Pore Size | Ring Characterization |
| --- | --- | --- |
| ZSM-35 | 4.2 Å × 5.4 Å | 10-1D |
| ZSM-22 | 4.4 Å × 5.5 Å | 8 × 10-2D |
| ZSM-23 | 4.5 Å × 5.2 Å | 10-1D |
| ZSM-48 | 5.3 Å × 5.6 Å | 10-1D |
| ZSM-5 | 5.3 Å × 5.6 Å | 10 × 10-3D |

The foregoing small pore size zeolites, like ZSM-5, are usually synthesized with Bronsted acid active sites by incorporating a tetrahedrally coordinated metal, such as Al, Ga, B, or Fe, within the zeolitic framework, employing highly siliceous materials or crystalline metallosilicate having one or more tetrahedral species having varying degrees of acidity. Their common ZSM-5 crystalline structure is readily recognized by a X-ray diffraction pattern described in U.S. Pat. No. 3,702,866 (Argauer, et al.) which is incorporated by reference thereto as if fully set forth herein.

In addition to the their restrictive small pore size, the effective catalysts for our process have a narrowly defined constraint index (CI) in the range from 3 to 10, but the CI alone is not indicative of their effectiveness. The CIs for the various effective catalysts, and that of ZSM-5, which is not effective despite being squarely within the range, are set forth in Table II herebelow.

TABLE II

| Catalyst | Constraint Index |
| --- | --- |
| ZSM-48 | 3.5 |
| ZSM-35 | 4.5 |
| ZSM-5 | 6.0 |
| ZSM-22 | 7.3 |
| ZSM-23 | 9.1 |

The dimerization catalysts used herein include only the small pore (i.e., about 4.2 Å–5.6 Å) shape-selective crystalline aluminosilicate zeolites having a silica-to-alumina ratio of at least 12, a constraint index of about 3.5 to 9.1 and significant Bronsted acid activity.

It is believed that the peculiar catalytic activity of the chosen catalysts with respect to conversion of propylene to hexenes, and isomerization of hexenes to tert-isohexenes, is closely related to their sorption rates for certain hydrocarbons, most notably 3-methylpentane and 2,2-dimethylbutane. The significance of these specific isomers redounds to their branched chain structure; and because the isomerization of hexenes to branched chain hexenes, and to tert-isohexenes in particular, is of especial interest herein. When the sorption rates, measured at 100° C., for the hydrocarbons listed in the following Table III are substantially exceeded, as they are for ZSM-5 (shown for comparison), the peculiar activity which characterizes the chosen catalysts, is palliated.

TABLE III

| | Sorption rate $\mu L/(gm)(sec^{0.5})$ at 100° C. | | | | |
| --- | --- | --- | --- | --- | --- |
| Component | ZSM-35 | ZSM-22 | ZSM-48 | ZSM-23 | ZSM-5 |
| n-$C_6$ | 26 | 30 | 32 | 44 | 50 |
| 3-methyl-$C_5$ | 3 | 9 | 11 | 13 | 38 |
| cyclohexane | <0.1 | <0.1 | 2 | 0.3 | 26 |
| 2,2-dimethyl$C_4$ | <0.1 | <0.1 | <0.1 | 0.1 | 6 |
| p-xylene | 3 | 6 | 6 | 5 | 8 |
| o-xylene | <0.1 | 1 | 0.2 | 0.5 | 3 |
| mesitylene | <0.1 | <0.1 | 0.1 | 0.2 | 0.7 |

As is clearly evident from the foregoing data, there is a close relationship between the lower sorption rates for the components identified above, and the desired activity exhibited by the chosen catalysts. ZSM-5 which has higher sorption rates, fails to meet the criteria. It is believed that the lower sorption rates of the chosen catalysts leads to more conversion to tert-isohexenes, and more selective isomerization of difficultly etherifiable isohexenes to easily etherifiable tert-isohexenes.

In particular, note that the sorption rates for 3-methyl-pentane (3-methyl$C_5$) for the chosen catalysts rise in small increments. From ZSM-35 to ZSM-22=6 $\mu L/(gm)(sec^{0.5})$, from ZSM-22 to ZSM-48=2, from ZSM-48 to ZSM-23=2, but from ZSM-23 to ZSM-5=25, a very large increase. For 2,2-dimethylbutane (2,2-dimethyl$C_4$) from ZSM-35 to ZSM-22 to ZSM-48=<0.1, from ZSM-48 to ZSM-23=0.1, but from ZSM-23 to ZSM-5=5.9, again a very large increase of more than an order of magnitude.

It is further believed that the peculiar activity of the chosen catalysts with respect to conversion to hexenes, and isomerization of hexenes to tert-isohexenes, is also closely related to their equilibrium sorption capacity (ESC) (cc/g). When the ESC for the hydrocarbons listed in the following Table IV is substantially exceeded, as they are for ZSM-5 (shown for comparison), the peculiar activity which characterizes the chosen catalysts, is diminished. Data for ZSM-35 is not currently available.

TABLE IV

| | Equilibrium Sorption Capacity (cc/g) at 100° C. | | | |
|---|---|---|---|---|
| Component | ZSM-22 | ZSM-48 | ZSM-23 | ZSM-5 |
| n-C$_6$ | 0.06 | 0.06 | 0.07 | 0.15 |
| 3-methyl-C$_5$ | 0.06 | 0.04 | 0.04 | 0.08 |
| cyclohexane | <0.01 | 0.02 | 0.01 | 0.07 |
| 2,2-dimethylC$_4$ | <0.01 | <0.01 | <0.01 | 0.08 |
| p-xylene | 0.04 | 0.05 | 0.04 | 0.08 |
| o-xylene | 0.02 | <0.01 | 0.01 | 0.07 |
| mesitylene | <0.01 | <0.01 | <0.01 | 0.02 |

Again, it is seen that the lower ESCs for the components identified above, appear to be determinative of the activity exhibited by the chosen catalysts. ZSM-5 which has higher ESCs fails to meet the criteria. It is believed that the lower ESCs of the chosen catalysts leads to more conversion to tert-isohexenes, and more selective isomerization of difficultly etherifiable isohexenes to easily etherifiable tert-isohexenes.

These sorption characteristics are set forth, in large part, in U.S. Pat. No. 4,810,357 for ZSM-22, ZSM-23, ZSM-35 and ferrierite. Their pore openings result in specific combi-nations of sorption properties, namely, (1) a ratio of sorption of n-hexane to o-xylene, on a volume percent basis, of greater than about 3, which sorption is determined at a P/Po of 0.1 and at a temperature of 50° C. for n-hexane and 80° C. for o-xylene; and, (2) by the ability to selectively crack 3-methylpentane (3MP) in preference to the doubly branched 2,3-dimethylbutane (DMB) at 1000° F. and 1 atmosphere pressure from a 1/1/1 weight ratio mixture of n-hexane/3-methyl-pentane/2,3-dimethylbutane, with the ratio of rate constants k3MP/kDMB determined at a temperature of 1000° F. being in excess of about 2.

The expression, "P/Po", is accorded its usual significance as described in the literature, for example, in "The Dynamical Character of Adsorption" by J. H. deBoer, 2nd Edition, Oxford University Press (1968) and is the relative pressure defined as the ratio of the partial pressure of sorbate to the vapor pressure of sorbate at the temperature of sorption. The ratio of the rate constants, k3MP/kDMB, is determined from 1st order kinetics, in the usual manner, by the following equation:

$$k = (1/Tc)\ln(1/1-\epsilon)$$

where k is the rate constant for each component, Tc is the contact time and $\epsilon$ is the fractional conversion of each component.

A chosen catalyst typically has an acid activity "$\alpha$" (alpha) above 5, preferably in the range from 5 to 150. The chosen catalyst is preferably supported on an inert support, for example a SiO2/Al2O3/clay matrix having a relatively low $\alpha$ in the range from 1 to 25. The $\alpha$ value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as $\alpha=1$ (rate constant=0.016 sec-−1). The $\alpha$ value for catalyst is defined by the specific test described in U.S. Pat. Nos. 3,827,968 and 3,960,978 to Givens et al, and in the Journal of Catalysis, Vol. 4, p. 527 (1965); Vol. 6, p. 278 (1966); and Vol. 61, p. 395 (1980), each of which references are incorporated by reference thereto as if fully set forth herein.

While suitable zeolites having silica: coordinated metal oxide molar ratio of 15:1 to 200:1 or higher may be used, it is advantageous to employ standard formulations for the chosen catalysts. These siliceous zeolites, per se, are well known in the art as is their manufacture, and since neither is especially relevant to the understanding of the invention claimed herein, no further description of them is included herein except by reference to the prior art disclosures.

The chosen catalysts can be effectively regenerated, are long-lived in operation, and display excellent stability under extreme conditions of operation. Conversion of C3=, and selectivity to dimer, each in an amount greater than 70% may be maintained with catalyst having a fresh $\alpha$ in the range from 15 to 150, preferably from 25-100.

The preparation and properties of the chosen catalysts are described in the following references which are incorporated by reference thereto as if fully set forth herein: ZSM-22 in U.S. Pat. No. 4,810,357 (Chester); ZSM-23 in U.S. Pat. Nos. 4,076,842 and 4,104,151; ZSM-35 in U.S. Pat. No. 4,016,245; and, ZSM-48 in U.S. Pat. No. 4,375,573.

Referring to FIG. 1 there is shown a reactor 10 in which the reaction zone may contain either a fixed bed or fluid bed of chosen catalyst. An olefinic, predominantly propylene stream 11, containing less than 2 mol % ethylene and a minor proportion by wt of propane, is fed to the reactor 10 where the stream 11 contacts the catalyst under dimerization conditions forming an effluent of dimerized product 12 with a conversion greater than 60%, preferably in the range from 75 to 95% or more. The effluent 12 is then cooled in a condenser 13 and flash-separated in flash drum 14 to recover the C$_6$ portion. Uncondensed gases, mainly propane and some unconverted propylene, are compressed by compressor 17 so that they may be led in stream 18 to storage, or purged. If deemed desirable to do so, a portion of the compressed gases may be recycled as stream 19 to the reactor 10, the remaining portion being led to storage or led off-site to a light ends unit.

The choice of specific unit operations for recovering the dimerized product and recycling a portion of the unreacted propylene, will depend upon the proportion of propylene and propane in the feed, the yield of hexenes from the dimerization reactor, etc. as is well known in the art.

In one preferred embodiment described above, where there is less than 20% by wt of propane in the feed, and the selectivity to hexenes is in the range from 60 to 80%, the effluent 12 is cooled in a heat exchanger 13 and flashed off in the flash drum 14 to yield a predominantly hexene stream 15. A portion of the unconverted light ends having a substantial amount of propylene when flashed from the drum is compressed and recycled.

It will be appreciated that the ratio of propylene to propane will govern the operating pressure conditions of the reactor, and if there is a substantial proportion of propane present, it may be desirable to compress and liquefy the stream 16, then fractionate the stream in a fractionator (not shown) to provide a desirable propylene content for recycle to the reactor.

Another preferred operation with plural (three in the drawing) reactors and without a recycle stream, is illustrated in phantom outline. The effluent 12' from first reactor 10A is flowed into second reactor 10B; the effluent 12" from reactor 10B is flowed to third reactor 10C; and the effluent 12"' from the third reactor 10C is cooled in the heat exchanger 13 and flashed off in flash drum 14 to yield a predominantly hexene stream 15.

It will be evident that if substantially pure propylene is used and the conversion is sufficiently high, a single reactor may be used without recycle. But where the C3 stream is a typical refinery stream containing up to 40% propane, then each reactor functions as a propene/propane fractionator. Since the propane is unreacted it flows through each of the several reactors, first one, then another, in series while the propene is dimerized, and too little propylene is left unreacted to justify recycling it.

An additional advantage of using plural reactors in series is that an active (e.g. $\alpha$ in the range 20–150 or higher) catalyst may be used in the first reactor under steady state process conditions to achieve the required degree of reaction severity. The catalyst in the second and/or third reactor(s) may be less active, for example, a coked or steamed catalyst with $\alpha$ less than 20 to obtain maximum conversion to tert-isohexenes.

The Integrated Dimerization and Etherification Process

Having produced the dimerized product as described above, a conventional etherification reaction may be used to produce the desired alkyl tert-hexyl ether by reaction with a lower ($C_1$–$C_5$) aliphatic alcohol. What is unobvious about our etherification process using a conventional oxygenate conversion catalyst is that the unreacted hexenes are recycled to the dimerization reactor to produce tert-isohexenes as a major portion by weight of the hexene isomers in the effluent of the reactor. This behavior of a chosen catalyst is surprisingly unlike that of ZSM-5 over which an olefin feed will equilibrate to form a common carbon number and olefin isomer distribution.

Such distribution occurs when unreacted hexenes or any mixture of $C_3=+$ olefins are reacted over the ZSM-5 catalyst which is known to yield a product which is essentially the same as that produced by feeding an essentially $C_3=$ stream over the catalyst (see Tables III and V in the Garwood article, supra). It is the failure to produce such a common carbon number distribution, but a mainly hexene stream typically containing less than about 15% by weight of cracked hexenes or $C_9+$ oligomers, which results in the unexpected benefits of recycling unreacted hexenes in the integrated process.

A conventional etherification catalyst may be used, such as a macroreticular cation exchange resin in the hydrogen form. An example of such a catalyst is "Amberlyst 15". Such a catalyst is preferably used at moderate temperatures below about 90° C., in the liquid phase at a pressure of about 200 psig. Equilibrium is more favorable at lower temperatures but the reaction rate decreases significantly. Excess methanol appears to be required to achieve acceptable selectivity over "Amberlyst 15" (see Chu et al, Industrial Engineering and Chemical Research, Vol. 26, No. 2, 1987, 365–369).

Instead of the foregoing resin catalyst, an acid medium-pore zeolite catalyst may be used to achieve highly selective conversion of iso-olefin and alcohol starting materials. Examples of such zeolite catalysts are ZSM-4, ZSM-5, ZSM-11, ZSM-12, ZSM-23, ZSM-35, ZSM-50 and zeolite Beta. Due to lower acidity as compared to resin catalysts, the zeolites need to be employed at higher reaction temperature to achieve the desired conversion rates. These solid acid catalyst particles are much more thermally stable than resin catalyst, are less sensitive to alkanol-to-isohexene ratio, give no acid effluent, and are easily and quickly regenerated (see Chu et al, "Preparation of Methyl tert-Butyl Ether (MTBE) over Zeolite Catalysts", Industrial Engineering and Chemical Research, op. cit.).

Figure 2:
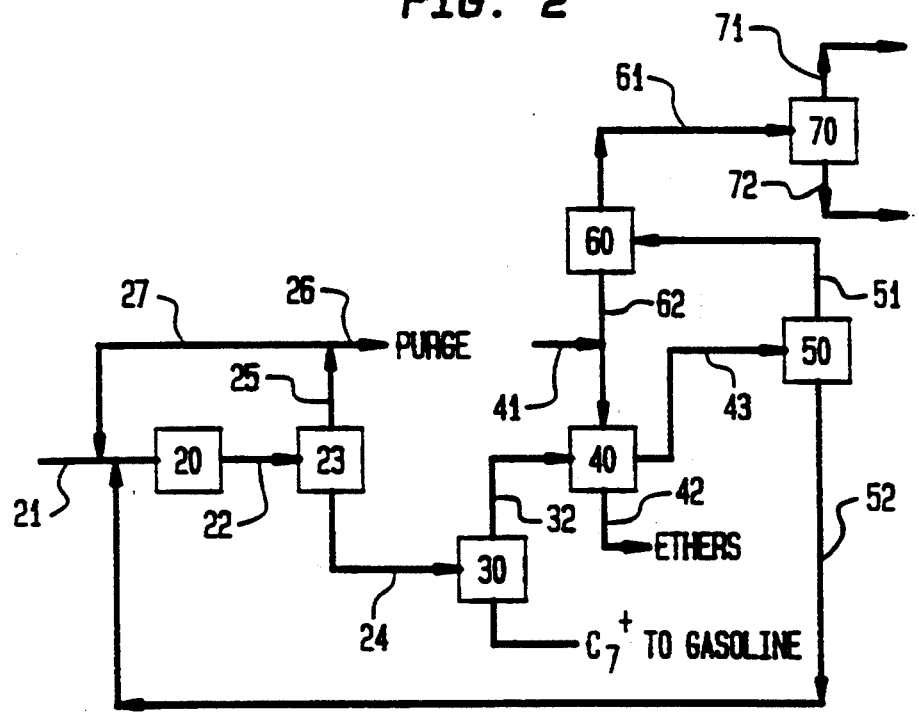
FIG. 2 is a diagrammatic flowsheet illustrating an integrated process in which the dimerization of propylene (shown in FIG. 1) is the first root process; the dimerized product is etherified in a second root process, and the unetherified hexenes are recycled to the reaction zone in the first root process.

Referring to FIG. 2, there is shown a dimerization reactor 20 (preferably a series of reactors such as 10A–10C in FIG. 1) through which a feed 21, in which there is preferably less than 2 mol % of a higher olefin than $C_3=$, is flowed under dimerization conditions to produce a dimerized product 22. The product 22 is cooled (as shown in FIG. 1 but not shown in FIG. 2) or otherwise liquefied, then flashed in drum 23 to recover its $C_4+$ content as stream 24. The lighter $C_3-$ components 25 are preferably not recycled but led away as stream 26 to a light ends plant on the site. If desired, a portion 27 containing sufficient propylene to justify recycling it, may be recycled to the reactor 20.

The stream 24 is flowed to a separation zone such as a splitter 30 from which the $C_{7+}$ components are removed as bottoms stream 31, and the $C_4$–$C_6$ taken as overhead stream 32. Stream 32 is flowed into an etherification zone 40 into which an alcohol stream 41 is introduced in a slight (5–25%) excess over stoichiometric to contact the etherification catalyst in zone 40 under suitable conditions which generate an optimum yield of etherate 42. The etherate 42 is the desired product which consists of more MHTE (methyl-hexyl-tert-ether) than any other ether such as MTBE or TAME.

Unetherified components in stream 43 are preferably flowed to a depentanizer 50. Unreacted alcohol, $C_4=$ and $C_5=$ taken overhead in stream 51 from the depentanizer 50 may be used as desired, for example, by first flowing the stream 51 to an alcohol fractionator 60 from which the methanol bottoms 62 is recycled to the etherification reactor 40. Making the separation of alcohol from combined $C_4=$ and $C_5=$ is rendered particularly simple and economical because of the process circumstances which cause these three components to be concentrated in a single stream. After separation from the stream, the combined $C_4=$ and $C_5=$ overhead 61 is flowed to a debutanizer 70. The $C_4=$ overhead 71 may be fed to an alkylation unit (not shown), and the $C_5=$ bottoms 72 blended into gasoline.

Bottoms from the depentanizer 50 consists essentially of unreacted hexenes, indicated by the hexene recycle stream 52, which is recycled to the dimerization reactor 20.

The effect of isomerizing (in the dimerization reactor) unreacted hexenes obtained as bottoms stream 52 (referred to as "hexene recycle") is evident in the following calculated values (from yields shown in Example 3) for the production of MHTE as a function of the ratio of hexene recycle: propene in the feed to the dimerization reactor 20.

|  | Recycle:$C_3=$ Feed Ratio (Wt/Wt) | | | |
| --- | --- | --- | --- | --- |
|  | None | 0.25:1 | 0.5:1 | 1:1 |
| $C_3=$ conversion | 72 |  |  |  |
| Total $C_6$ gasoline | 34 | 25 | 17 | 6 |
| tert-$C_6=$ in gasoline | 18 | 14 | 9 | 2 |
| MHTE | 26 | 37 | 49 | 65 |

The following examples provide specific illustrations for two of the chosen catalysts.

EXAMPLE 1

An essentially pure propylene feed diluted with an equal volume of helium is flowed over ZSM-35 zeolite CI 4.5, and $\alpha=125$, on a silica-alumina support (79.5% ZSM-35, 20.5% SIO2/Al2O3) at WHSV 3.1 hr−1 and 1 atm., in a fixed bed reactor maintained at 500° F. The following are the results:

TABLE V

|  | Yield | Selectivity |
|---|---|---|
| $C_3=$ Conversion Product Distribution, wt % | 40.5 | — |
| $C_5^-$ saturates | 0.9 | 2.2 |
| $C_5^-$ olefins | 2.7 | 6.7 |
| $C_6$ olefins | 33.5 | 82.7 |
| $C_7^+$ | 3.4 | 8.4 |

It is evident that propylene conversion at this relatively low temperature of 260° C. is only about 40% but the high selectivity to the dimer is surprising.

EXAMPLE 2

An essentially pure propylene feed is flowed through a fixed bed of alumina-bound ZSM-23 extrudate (65% ZSM-23, 35% Al2O3), steamed to $\alpha=7$, at WHSV=8 hr$^{-1}$ and 30 psig (307 kPa), in a reactor maintained in three separate runs at temperatures in the range from 550°–650° F. (288°–343° C). The following are the results:

TABLE VI

|  | Run 1 | Run 2 | Run 3 |
|---|---|---|---|
| Temp. °F. | 650 | 600 | 550 |
| $C_3=$ conversion, wt % | 94.6 | 94.4 | 88.6 |
| Product selectivities, wt % |  |  |  |
| $C_6^+$ | 86 | 93 | 97 |
| $C_6=$ | 53 | 60 | 64 |
| tertiary $C_6=$ | 43 | 49 | 50 |
| $C_5^-$ saturates | 0.9 | 0.2 | 0.2 |

It is evident that the above process conditions with the use of ZSM-23 provide very high selectivities to $C_6=$ dimer while maintaining a propylene conversion of about 90%. The $C_6=$ dimer accounts for over 60% by wt of the $C_6=$ content of the reactor effluent. Though the selectivity of the ZSM-23 is not as high as that of ZSM-35 under conditions tested, the conversion is significantly higher.

EXAMPLE 3

An essentially pure propylene feed is flowed through a fluid bed of ZSM-35 zeolite CI 4.5, but with unsteamed $\alpha=22$, on a silica-alumina-clay support (25% ZSM-35, 75% SiO2/Al2O3/-clay) at WHSV 8 hr− and 31 psig (314 kPa), in a reactor maintained at 743° F. (395° C). Field ionization mass spectrographic analysis provides the following results:

TABLE VII

|  | Saturates | Aromatics | Olefins | Total |
|---|---|---|---|---|
| $C_1$ | — | — | — | — |
| $C_2$ | 0.3 | — | — | 0.3 |
| $C_3$ | 0.3 | — | 28.2 | 28.5 |
| $C_4$ | 0.1 | — | 2.9 | 3.0 |
| $C_5$ | 0.2 | — | 2.9 | 3.1 |
| $C_6$ | 1.2 | — | 51.2 | 52.4 |
| $C_7$ | — | — | 2.1 | 2.1 |
| $C_8$ | — | — | 1.2 | 1.2 |
| $C_9$ | — | 0.1 | 7.6 | 7.7 |
| $C_{10}$ | — | 0.1 | 0.4 | 0.5 |
| $C_{11}$ | — | — | 0.1 | 0.1 |
| $C_{12}$ | — | — | 1.1 | 1.1 |
| Total | 2.1 | 0.2 | 97.7 | 100.0 |

It is evident from the foregoing data that at elevated temperature of about 400° C. conversion of $C_3=$ is greater than 70%, yet the selectivity to dimer is 71%. The product is essentially linear olefinic with saturates and aromatics limited to about 2.3%.

The following Table VIII sets forth the GC analysis of the hexenes in the product dimer made in the foregoing Example 3, side-by-side with a typical analysis from hexenes produced in a commercially available process (Dimersol), which analysis was published in "Meeting Lead Phasedown Octane Requirements with Dimate" by J. W. Andrews, 1985 NPRA Annual Meeting, AM-85-45.

TABLE VIII

| Component | Content, wt % | |
|---|---|---|
|  | Ex. 3 | Dimersol |
| 1-$C_6=$ | 1.0 | — |
| 2-$C_6=$, cis | 3.8 | 5.8 |
| 2-$C_6=$, trans | 7.8 | 13.3 |
| 3-$C_6=$, cis + trans | 4.7 | 4.0 |
| 2-methyl-1-$C_5=$* | 9.3 | 4.7 |
| 3-methyl-1-$C_5=$ | 1.6 | — |
| 4-methyl-1-$C_5=$ | 1.3 | 2.3 |
| 2-methyl-2-$C_5=$* | 21.9 | 19.4 |
| 3-methyl-2-$C_5=$, cis* | 11.9 | — |
| 3-methyl-2-$C_5=$, trans+* | 20.2 | — |
| 4-methyl-2-$C_5=$, cis | 1.8 | 6.7 |
| 4-methyl-2-$C_5=$, trans | 5.8 | 36.9 |
| 2-ethyl-1-$C_4=$* | 2.9 | — |
| 2,3-dimethyl-1-$C_4=$* | 1.9 | 4.7 |
| 3,3-dimethyl-1-$C_4=$ | — | — |
| 2,3-dimethyl-2-$C_4=$* | 4.1 | 2.2 |
| Total | 100 | 100* |
| Total tert-isohexenes | 72.2 | 31.0 |

From the foregoing it is evident that the amount of the total tert-isohexenes in the dimer product is nearly two and one-half times as much as the amount present in Dimersol. This preponderance of tert-isohexenes obtained in our process results in the facile and economical production of etherate having a major proportion by weight of MHTE. Since the etherate contains a substantial amount of 2,3-dimethyl-2-butene and of 2,3-dimethyl-1-butene the value of the etherate for blending into gasoline is enhanced. Ethers of each of the foregoing tert-isohexenes provides a higher boost in octane than the ethers of most of the other tert-isohexenes whether internal or external.

The RON blending octane number of the ethers of the tert-isohexenes range from about 101–111. The MON blending octane number of the ethers of the tert-isohexenes range from about 91–98. The Reid vapor pressure of the ethers range from about 1.1 psig to about 1.3 psig, which is highly desirable for blending the ethers into gasoline.

EXAMPLE 4

Data were obtained to show the effect of the use of ZSM-35 to selectively convert propylene to tertiary hexenes. The effect of temperature on propylene ($C_3=$) conversion and product selectivity was examined to compare the disclosure of Plank et al, U.S. Pat. No. 3,992,466, the contents of which are incorporated herein by reference, which showed in Example 4 effective oligomerization of propylene to $C_5+$ products at 600° F. Results of comparative experiments are depicted in Table IX below and show that temperature has a significant impact on yields. An approximately 100° F. temperature window, 357°–413° C. (675°–775° F.) exists where propylene conversion and tert-hexenes are maximized. Below this, the reaction is kinetically limited; above, backcracking to $C_3=$ becomes extensive. This effect outweighs the observation that selectivity to hexenes (c. 60%) and tert-hexenes (40–50%) are fairly constant below about 410° C. (770° F.) where limited olefin scrambling reactions take place. At 600° F., propylene conversion would be less than 50%, giving an overall tert-hexene yield of about 20%.

The ZSM-35 catalyst used was synthesized following procedures similar to Example 1 of the Plank reference. The zeolite was precalcined in nitrogen at 540° C. (1000° F.) for 3 hours, exchanged with 1N ammonium nitrate solution at room temperature for 1 hour (5 ml solution/g zeolite), drained and exchanged a second time, washed with deionized water, dried at 121° C. (250° F.), and finally, calcined in air at 540° C. (1000° F.) for 6 hours. The hydrogen form zeolite was then pelleted and sized to 14/25 mesh. The alpha value of the finished material was 113; sodium content was 63 ppm. The catalyst was evaluated in a fixed bed pilot unit operated under atmospheric pressure and 8 WHSV with 100% propylene feed. Temperatures varied from 260°–427° C. (500°–800° F.).

TABLE IX

| | Effect of Temperature on $C_3=$ Conversion Over ZSM-35 | | | |
|---|---|---|---|---|
| Temp., °C. | $C_3=$ Conv, Wt % | Selectivity to $C_6=$, Wt % | Tert $C_6$/ Tot $C_6=$, Wt % | Tert-$C_6=$ Yield (Sel), Wt % |
| 261 | 36.1 | 59.5 | 75.6 | 16.2 (45) |
| 325 | 50.0 | 65.5 | 70.9 | 23.2 (46) |
| 358 | 81.9 | 66.5 | 72.7 | 39.6 (48) |
| 409 | 86.2 | 58.5 | 73.0 | 42.7 (50) |
| 419 | 77.7 | 49.6 | 71.1 | 27.4 (35) |

NOTE: Large exotherm was obtained from the $C_3=$ dimerization reaction. Temperature shown is the average of the hottest portion of the catalyst bed where the bulk of the reaction took place.

It will now be evident that the chosen catalysts have the unique ability, under the stated process conditions, to dimerize propylene so as to provide a much larger amount of tert-isohexenes than one might expect to generate with a zeolite catalyst known to have oligomerization activity; and to recover the dimer easily. It is this unique ability of a chosen catalyst which makes it economical to etherify the dimer so recovered, and use it to produce a blended gasoline which benefits from the high octane contributed by ethers of tert-isohexenes. Though the contribution of such ethers was known, there was no economical way to provide the hexenes with etherifiable carbon atoms.

Having thus clearly and objectively stated the problem to be solved, and its solution by the invention disclosed herein, and having provided a detailed description and illustrations of the best mode of practicing the invention, it is to be understood that no undue restrictions are to be imposed by reason thereof, and particularly, that the invention is not restricted to a slavish adherence to the details set forth herein.

What is claimed is:

1. A process for the production of isomers of hexene from propylene, comprising, (a) feeding a propylene-rich feed substantially free of lower and higher olefins into a dimerization reaction zone, (b) contacting said feed in a reaction zone maintained at a pressure in the range from 0.1 to 10 atm., and a temperature in the range from 232° C.–426° C. (450°–800° F.), said reaction zone containing enough catalyst to effect dimerization of a major proportion by weight of the propylene content of said feed, said catalyst characterized by the shape selectivity of a small-pore zeolite having a 10-membered ring structure, said zeolite being ZSM-23; (c) flowing said feed through said reaction zone at a weight hourly space velocity (WHSV) based on olefins, in the range from 0.1 to 30 $hr^{-1}$; and, (d) converting at least 40% by weight of said propylene to a dimer product containing a major proportion by weight of hexene isomers, more than 50% by weight of which hexene isomers are tert-isohexenes.

2. The process of claim 1 wherein said propylene-rich feed contains less than about 40 mol % propane, less than 2 mol % ethylene and less than 5 mol % of butenes and higher olefins; and, a per pass selectivity of propylene converted to $C_6=$ of at least 30% by weight is obtained.

3. The process of claim 1 wherein said small pore zeolite has a sorption rate for 2,2-dimethylbutane no greater than about 0.1 $\mu L/(gm)(sec^{0.5})$, and a sorption rate for 3-methylpentane no greater than about 13 $\mu L/(gm)(sec^{0.5})$; said reaction zone is maintained at a temperature in the range of about 288°–340° C. (550°–650° F.) and, obtaining a per pass selectivity of propylene converted to $C_6=$ of at least 50% by weight is obtained.

4. The process of claim 2 wherein said small pore zeolite has an equilibrium sorption capacity for 2,2-dimethylbutane no greater than about 0.01 cc/gm, and an equilibrium sorption capacity for 3-methylpentane no greater than about 0.06 cc/gm; and, a per pass selectivity of propylene converted to $C_6=$ of at least 50% by weight is obtained.

5. The process of claim 2 including separating the $C_4+$ components from said dimer product and recycling a portion of separated $C_3$ components to said reaction zone.

6. The process of claim 2 wherein said reaction zone includes plural reaction zones through which said propylene-rich feed is flowed, first through one zone, then through another zone, and no portion of said dimer product lighter than $C_4$ is recycled to said reaction zone.

7. The process of claim 2 wherein at least one of (a) conversion of $C_3=$ in said reaction zone and (b) per pass selectivity in the formation of $C_6$ olefins, is greater than 50%.

8. The process of claim 2 wherein said dimer product consists essentially of a major proportion by weight of tert-isohexenes.

9. The process of claim 2 wherein said small pore zeolite has the structure of ZSM-23 and is on an alumina support (65% ZSM-23, 35% Al$_2$O$_3$) having an α value in the range from 5 to about 50, said temperature is in the range from about 232°–400° C. (450°–750° F.), said pressure is in the range from about 240–450 kPa (20–50 psig), and said WHSV is in the range from about 5–10 hr$^-$ (based on olefin) to produce a C$_3$$^=$ conversion in the range from about 85–95% by weight, and a selectivity to tert-isohexenes in the range from about 40 to 50% by weight.

10. An integrated process for the production of ethers of tert-hexenes containing a major portion by weight of ethers of tert-isohexenes, said process comprising, a first root process comprising dimerizing a propylene-rich stream to form a tert-isohexene-rich stream, and, a second root process comprising etherifying tert-isohexenes with a lower primary or secondary C$_1$–C$_5$ aliphatic alcohol to form ethers; said first root process comprising, (a) feeding a propylene-rich feed essentially free of lower and higher olefins into a dimerization reaction zone, (b) contacting said feed with a catalyst characterized by the shape selectivity of a small-pore zeolite having a 10-membered ring structure, said zeolite being selected from the group consisting of ZSM-22, ZSM-23, ZSM-35 and ZSM-48 at a pressure in the range from 0.1 to 10 atm., and a temperature in the range from 232° C.–426° C. (450°–800° F.); (c) flowing said feed through said dimerization zone at a weight hourly space velocity (WHSV) based on olefins, in the range from 0.1 to 30 hr$^{-1}$; and, (d) converting at least 40% by weight of said propylene to a dimer product containing a major proportion by weight of hexene isomers more than 50% by weight of which are tert-isohexenes; and, said second root process comprising, (e) reacting said tert-isohexene-rich stream with said alcohol in the presence of an acid etherification catalyst under reaction conditions in an etherification zone effective to produce a mixture of tert-alkyl ethers; (f) removing a mixture of unreacted hexenes and alcohol from said etherification zone and recycling a stream consisting essentially of the unreacted hexenes to the dimerization reaction zone to produce a mixed stream of C6 olefins comprising tert-isohexenes without substantially cracking the unreacted hexenes or generating higher molecular weight products; (g) recovering an ether-rich effluent essentially free of propylene, together with unreacted alkenes and unreacted alcohol; and, (h) recovering said mixture of tert-alkyl ethers.

11. The process of claim 10 wherein step (d) comprises obtaining a per pass selectivity of propylene converted to C$_6$$^=$ of at least 30% by weight; said propylene-rich feed contains less than about 40 mol % propane, less than 2 mol % ethylene and less than 5 mol % of butenes and higher olefins; and said alcohol used in step (e) is a primary C$_1$-C$_3$ aliphatic alcohol.

12. The process of claim 10 wherein step (d) comprises obtaining a per pass selectivity of propylene converted to C$_6$$^=$ of at least 50% by weight; said small pore zeolite has a sorption rate for 2,2-dimethylbutane no greater than about 0.1 μL/(gm) (sec$^{0.5}$), and a sorption rate for 3-methylpentane no greater than about 13 μL/(gm)(sec$^{0.5}$ ).

13. The process of claim 10 wherein step (d) comprises obtaining a per pass selectivity of propylene converted to C$_6$$^=$ of at least 50% by weight; said small pore zeolite has an equilibrium sorption capacity for 2,2-dimethylbutane no greater than about 0.01 cc/gm, and an equilibrium sorption capacity for 3-methylpentane no greater than about 0.06 cc/gm.

14. The process of claim 10 including separating the C$_4$+ components from said dimer product and recycling a portion of separated C$_3$ components to said reaction zone.

15. The process of claim 10 wherein said reaction zone includes plural reaction zones through which said propylene-rich feed is flowed, first through one zone, then through another zone, and no portion of said dimer product lighter than C$_4$ is recycled to said reaction zone.

16. The process of claim 10 wherein at least one of (a) conversion of C$_3$$^=$ in said reaction zone and (b) selectivity in the formation of C$_6$ olefins, is greater than 50%.

17. The process of claim 10 wherein said dimer product consists essentially of a major proportion by weight of tert-isohexenes.

* * * * *

UNITED STATES PATENT AND TRADEMARK OFFICE
CERTIFICATE OF CORRECTION

PATENT NO. : 5,434,327
DATED : July 18, 1995
INVENTOR(S) : Arthur A. Chin et al

It is certified that error appears in the above-indentified patent and that said Letters Patent is hereby corrected as shown below:

Col. 16, line 27 (claim 3), delete "obtaining"

Col. 17, line 6 (claim 9), "hr-" should read --$hr^{-1}$--.

Col. 17, line 6 (claim 9), "$C_3^-$" should read --$C_3^=$--.

Signed and Sealed this

Nineteenth Day of September, 1995

Attest:

BRUCE LEHMAN

*Attesting Officer*  *Commissioner of Patents and Trademarks*